(12) United States Patent
Harrison

(10) Patent No.: US 9,164,056 B2
(45) Date of Patent: Oct. 20, 2015

(54) SYSTEM AND METHOD FOR DETECTING USED AND DRIED SENSORS

(75) Inventor: Bern Harrison, Granger, IN (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 531 days.

(21) Appl. No.: 13/600,441

(22) Filed: Aug. 31, 2012

(65) Prior Publication Data

US 2014/0027308 A1  Jan. 30, 2014

Related U.S. Application Data

(60) Provisional application No. 61/676,549, filed on Jul. 27, 2012.

(51) Int. Cl.
*G01N 27/327* (2006.01)
*G01N 27/04* (2006.01)
*A61B 5/145* (2006.01)
*A61B 5/1486* (2006.01)

(52) U.S. Cl.
CPC .......... *G01N 27/3274* (2013.01); *A61B 5/1486* (2013.01); *A61B 5/14532* (2013.01); *A61B 5/14535* (2013.01); *G01N 27/04* (2013.01); *A61B 2560/028* (2013.01)

(58) Field of Classification Search
CPC ..... G01N 27/48; G01N 27/26; G01N 27/327; G01N 27/3273; G01N 27/49; G01N 27/80
See application file for complete search history.

(56) References Cited

U.S. PATENT DOCUMENTS

| | | | |
|---|---|---|---|
| 2005/0284757 A1* | 12/2005 | Allen | 204/400 |
| 2006/0175205 A1 | 8/2006 | Cui et al. | |
| 2007/0017824 A1 | 1/2007 | Rippeth et al. | |
| 2008/0000779 A1 | 1/2008 | Wang et al. | |
| 2008/0248581 A1* | 10/2008 | Chu et al. | 436/66 |
| 2010/0169035 A1* | 7/2010 | Liang et al. | 702/65 |

FOREIGN PATENT DOCUMENTS

WO   WO 2011/012848   * 2/2011

OTHER PUBLICATIONS

International Search Report and Written Opinion, PCT/US2012/053390, date Jan. 25, 2013.

* cited by examiner

*Primary Examiner* — Jennifer Dieterle

(57) ABSTRACT

Systems and methods for detecting dried test strips are provided, where a dried test strip may be one that has been re-inoculated with a biological sample after having already been previously inoculated with another sample at an earlier time (e.g., hours or days before). In various aspects, a biosensor such as an amperometric glucose biosensor ("meter") may apply one or more input electrical signals to an inoculated test strip having at least a pair of electrodes in contact with the biological sample. The meter may measure output current value(s) resulting in response to the input electrical signals applied to the test strip. The meter may determine whether the test strip is a dried test strip by comparing a ratio of the measured output current value(s) with a boundary ratio value.

18 Claims, 6 Drawing Sheets

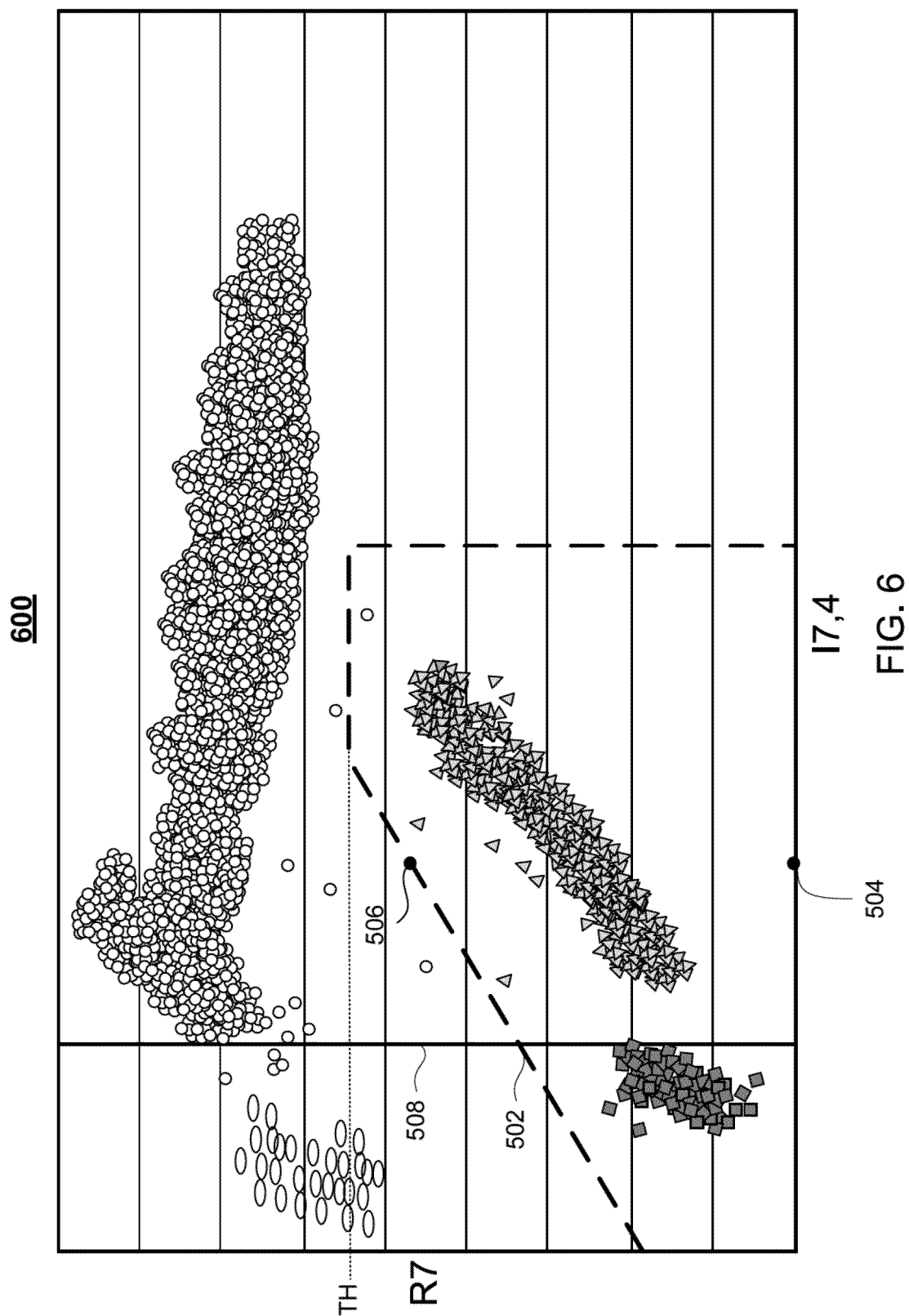

SYSTEM AND METHOD FOR DETECTING USED AND DRIED SENSORS

CROSS-REFERENCE TO RELATED APPLICATIONS

The present application claims the benefit of the filing date of U.S. Provisional Patent Application No. 61/676,549 filed Jul. 27, 2012, the disclosure of which is hereby incorporated herein by reference.

FIELD OF INVENTION

The present disclosure is generally directed to the field of medical devices. More specifically, this disclosure relates to apparatus and methods for measuring the amount of an analyte in a sample of bodily fluid, such as those used to measure glucose in a sample of whole blood.

BACKGROUND OF THE INVENTION

An amperometric glucose biosensor typically uses a sensor commonly referred to as a "test strip" having at least a pair of electrodes including a working electrode and a counter electrode. The test strip also includes a dry reagent in contact with the working electrode and counter electrode, and a capillary flow channel extending from an inlet opening to the working and counter electrodes. The reagents typically include an enzyme that is capable of oxidizing the glucose in the sample, such as glucose oxidase and one or more mediators adapted to reoxidize the reduced enzyme resulting from oxidation of the glucose, thereby forming a reduced mediator. The test strip is inserted into a meter so that the working and counter electrodes are electrically connected to the components within the meter. After the test strip is inserted in the meter, a sample of a bodily fluid such as blood is introduced into the capillary flow channel and contacts the working electrode, counter electrode and reagent, whereupon the components within the meter apply one or more electrical voltages between the working and counter electrodes, and measure the electrical current passing between the electrodes. The reduced mediator is oxidized at the working electrode, thereby producing a measurable current which is related to the amount of reduced mediator present at the working electrode, and therefore related to the concentration of glucose in the fluid. The measured current typically begins at a high value and then declines and approaches a constant value. For example, the current measured at a predetermined time during application of a voltage may be used to determine the glucose content of the sample.

Users will occasionally attempt to conduct a blood glucose test with a previously used test strip. Such re-use will yield erroneous readings. To prevent re-use, the meter can be arranged to measure conductivity between the electrodes of the strip prior to introduction of a fluid sample. When the strip is inserted into the meter, the electrical components within the meter apply a voltage between the electrodes and measure current flow. A new, unused test strip has only the dry reagent between the electrodes, and therefore has a very high electrical resistance between the electrodes prior to application of a fluid sample. However, a previously-used test strip which is still wet with the previous sample will show a very low electrical resistance between the electrodes and a high current flow. The meter can easily recognize this and emit a warning, terminate the test, or both. However, if the original use of the strip occurred many hours or days previously, the prior fluid sample will have dried. In this case, the conductivity test by the meter will not reveal the problem.

Reuse of previously used, dried test strips can lead to erroneous readings. For example, readings from such used test strip would likely have a very large negative bias due to the loss of chemistry from the working and/or the counter electrode due to the prior use. Thus, further improvement would be desirable.

SUMMARY OF THE INVENTION

Various aspects of the systems and methods disclosed herein may be implemented in hardware, software, or a combination of both. Systems and method for detecting and reporting reuse of previously inoculated dried test strips are provided. In various aspects, a system and method are provided to determine that a test strip is a dried test strip that has been re-inoculated with a sample after already having been inoculated with another sample at an earlier time, determine a glucose reading from a test strip inoculated with a blood sample, and correct a measured glucose reading based on factors such as the ambient temperature of the blood sample and the amount of hematocrit determined from the blood sample.

A method for detecting reuse of a test strip in a biosensor is provided. The method includes inoculating a test strip having a dry reagent and a plurality of electrodes including a bare electrode which is normally not in contact with the dry reagent with a liquid so that the liquid contacts the dry reagent, the bare electrode and one or more other electrodes. The method further includes applying an electrical potential between the bare electrode and one or more of the other electrodes while the electrodes are in contact with the liquid, and measuring a current flow between the bare electrode and one or more of the other electrodes responsive to application of the potential. The method further includes determining, based on one or more parameters of the measured current flow, whether the sensor strip is one that has been previously wetted and dried before the inoculating step.

In one aspect, a first current value at a first time during the potential applying step and a second current value at a second, later time during the potential applying step may be measured.

A ratio between the second current value and the first current value may be calculated, and the ratio may be compared with a boundary ratio value. In one aspect, the boundary ratio may be selected based at least in part on a current value measured during the potential-applying step. Furthermore, the boundary ratio may be selected at least in part on one of the first and second current values.

In one aspect, the boundary ratio may be the ratio of the second current value divided by the first current value, and a determination may be made that the sensor strip is one that had been previously wetted and dried when the ratio is less than or equal to the boundary ratio value.

In one embodiment, the one or more other electrodes on the strip may include a working electrode a counter electrode, and the method may further include applying at least one input electrical signal between the working electrode and the counter electrode. At least one output signal resulting in response from application of the at least one input electrical signal may be measured, and a concentration of the analyte in the sample based at least in part on the at least one output signal may be determined. In one aspect, the input electrical signal may be a potential and the output electrical signal may be a current flowing between the working and counter electrodes.

The determined concentration of the analyte in the sample may be corrected based at least in part on at least one parameter of the measured current flow. In one embodiment, for example, the liquid may be blood and the concentration of the analyte may be corrected for an effect related to hematocrit. In accordance with this embodiment, the analyte may be glucose and the dry reagent may further include an enzyme reactive with glucose and a mediator.

In a yet another aspect, the method may include comparing a current value measured during the potential-applying step with a threshold current. A determination may then be made based on the comparison as to whether the sensor strip is one that has been previously wetted with blood and dried before the inoculating step as opposed to one that has been previously wetted with water and dried before the inoculating step.

A biosensor for detecting reuse of a test strip is provided. The biosensor may include a processor and a memory storing one or more executable instructions. The instructions, when executed by the processor, may configure the processor to apply an electrical potential between a bare electrode and one or more other electrodes of a test strip while the electrodes of the test strip are in contact with a liquid, the test strip having a dry reagent and the bare electrode being normally not in contact with the reagent; measure a current flow between the bare electrode and one or more of the other electrodes responsive to application of the potential; and determine, based on one or more parameters of the measured current flow, whether the sensor strip is one that has been previously wetted and dried before inoculation of the test strip with the liquid.

A non-transitory computer-readable storage unit on which computer readable instructions of a program are stored is provided. The instructions, when executed by a processor, may cause the processor to apply an electrical potential between a bare electrode and one or more other electrodes of a test strip while the electrodes of the test strip are in contact with a liquid, the test strip having a dry reagent and the bare electrode being normally not in contact with the reagent; measure a current flow between the bare electrode and one or more of the other electrodes responsive to application of the potential; and determine, based on one or more parameters of the measured current flow, whether the sensor strip is one that has been previously wetted and dried before inoculation of the test strip with the liquid.

BRIEF DESCRIPTION OF THE FIGURES

FIG. 6 is a graph depicting certain results in accordance with another aspect of the disclosure.

DETAILED DESCRIPTION

Figure 1:
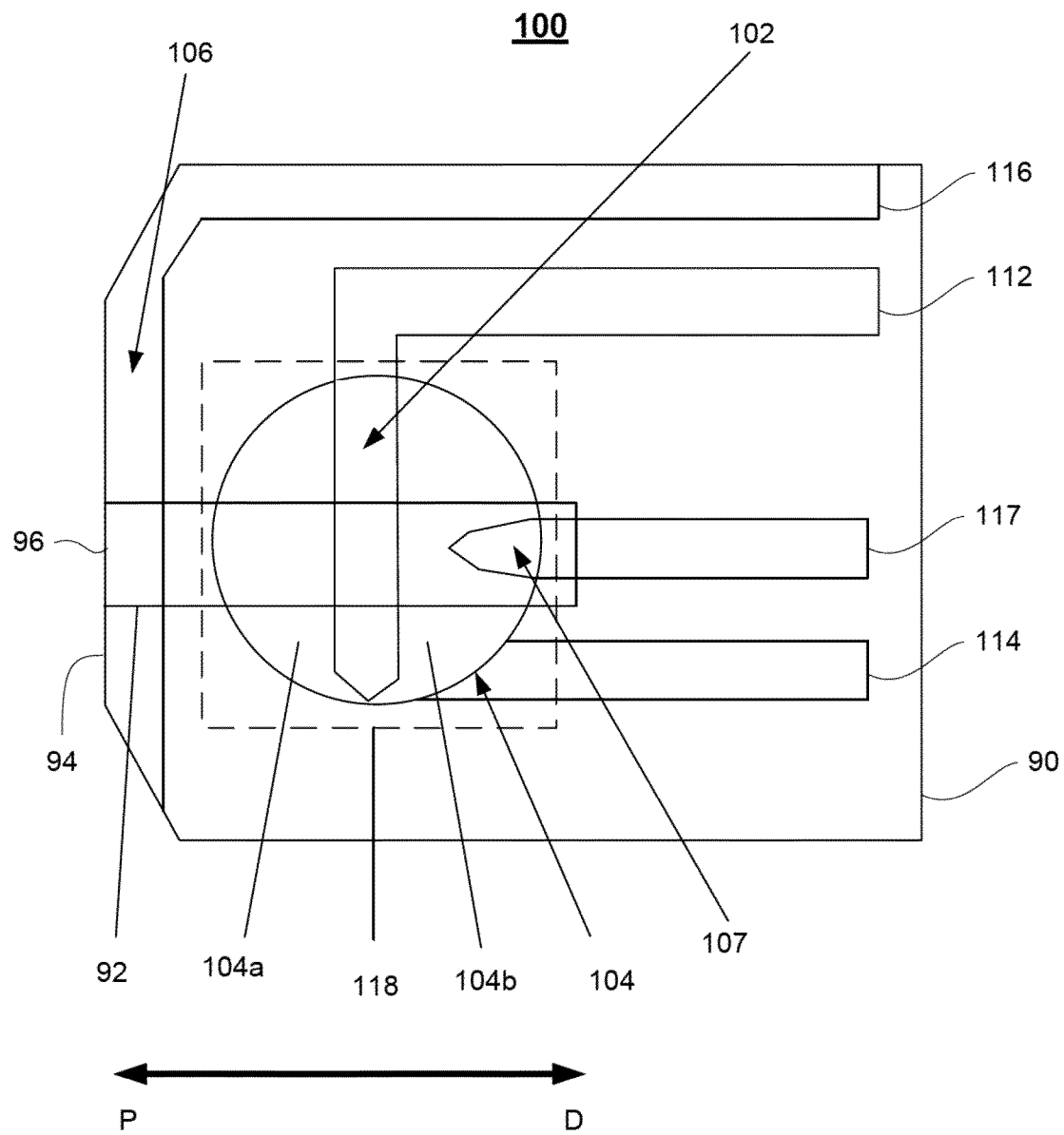
FIG. 1 is a schematic plan view of a test strip in accordance with an embodiment of the invention.
Figure 2:
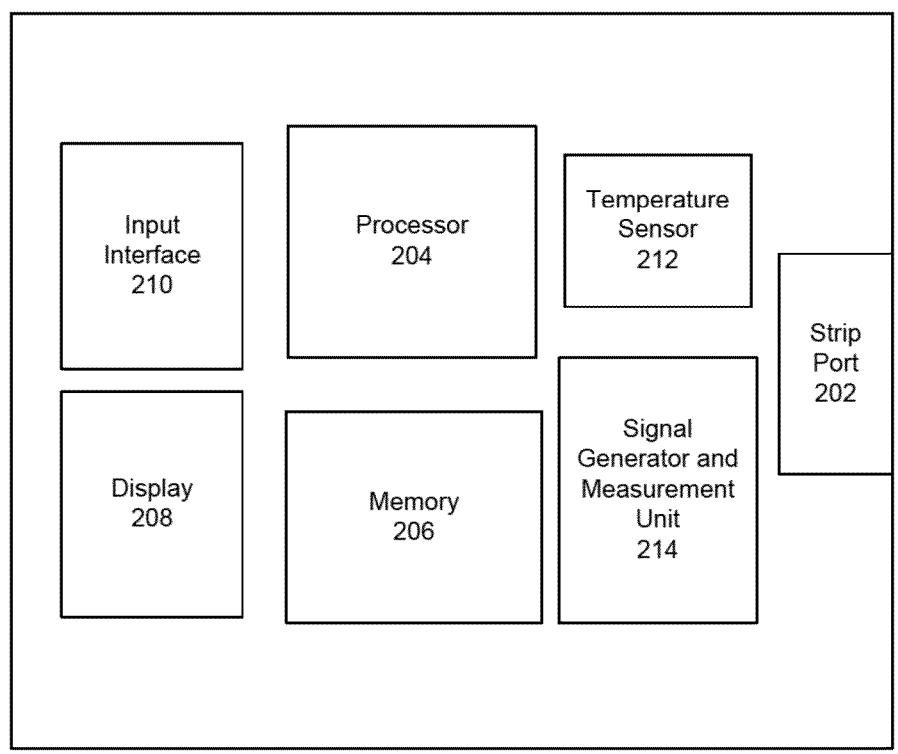
FIG. 2 is a block diagram of an amperometric biosensing meter in accordance with an embodiment of the invention.

FIGS. 1-2 respectively illustrate an example of a test strip 100 and a meter 200 in accordance with various aspects of the invention. While particular configurations of a meter and test strip are shown, the disclosure is not limited to any particular configuration.

A test strip 100 used in one embodiment of the invention includes a body 90 defining a capillary flow channel 92 extending from one edge 94 of the body 90. The flow channel 92 has an inlet opening 96 which constitutes a proximal end of the flow channel 92. Stated another way, the flow channel 92 defines a proximal direction P and distal direction D as indicated in FIG. 1. For example, body 90 may be constructed as a laminate including a bottom layer, a spacer layer having a gap defining the flow channel 92, and a top layer covering the spacer layer. Merely by way of example, capillary flow channel 92 may have a width of about 1.2 mm or less and a height (in a direction perpendicular to the plane of the drawing in FIG. 1) of about 0.1 mm or less.

The test strip also includes a plurality of electrodes carried on body 90. For example, the electrodes may be formed as conductive metallic films on the bottom layer of the body. For example, the metallic films may include palladium at the surfaces of the films exposed to the channel and hence exposed to the sample liquid during use. The electrodes include a working electrode 102 and a counter electrode 104, which extend across the flow channel 92 in close proximity to one another. In the particular embodiment depicted, counter electrode 104 includes a portion 104a disposed proximal to working electrode 102 and a portion 104b distal to the working electrode. Electrodes 102 and 104 are connected to terminals 112 and 114, respectively. Chemistry, such as a dry reagent including an enzyme (e.g., glucose oxidase) reactive with an analyte (e.g., glucose) in a biological sample (e.g., blood) and a mediator (a compound susceptible to reduction and oxidation) is provided within a predefined region 118 of the strip so that the reagent contacts and desirably covers both the working electrode 102 and the counter electrode 104 within the predefined region. In another embodiment, the dry reagent may also include glucose dehydrogenase with FAD cofactor ("FAD-GDH"). Other enzymes suitable for measurement of glucose include glucose dehydrogenase with NAD or PQQ cofactors, and hexokinase.

The test strip 100 according to this embodiment also includes a bare electrode 106, also referred to herein as a "hematocrit" electrode. Bare electrode 106 extends across the flow channel 92 at a location proximal to the working electrode 102 and the counter electrode 104 and outside of the region 118 occupied by the dry reagent. Although the bare electrode 106 is disposed outside of the region 118 occupied by the dry reagent, the bare electrode desirably is close to region 118. Merely by way of example, the distal edge of the bare electrode may be disposed less than about 0.3 mm from region 118, and less than about 0.6 mm from the proximal edge of working electrode 104. In the unused condition depicted in FIG. 1, bare electrode 106 is free of any chemistry. The dry reagent in region 118 is absent from the bare electrode 106 prior to inoculation of the test strip with a liquid sample such as blood. Bare electrode 106 is electrically connected to a contact terminal 116.

The test strip according to this embodiment further includes a detection electrode 107 disposed in the channel 92 at the distal edge of counter electrode 104. The detection electrode is connected to a further terminal 117. The detection electrode is covered by the dry reagent 118. The detection electrode can be used to determine when a liquid has filled channel 92 to a point distal to the working electrode and counter electrode, and can also be used as a portion of the counter electrode 104.

In addition to the electrodes shown in FIG. 1, the test strip 100 may include other electrodes (not shown), such as additional counter, working, or bare electrodes.

The meter 200 (FIG. 2) includes a strip port 202 for receiving the test strip 100. The strip port 202 is arranged to electrically couple one or more components of the meter 200 with the terminals 112, 114, 116 and 117 on the test strip 100, and thus couple the components of the meter to the electrodes 102, 104, 106 and 107. Thus, the strip port 202 includes contacts (not shown) arranged to engage the terminals 112, 114, 116 and 117 of the strip 100.

The meter 200 may operate under control of a processor 204. The processor 204 may be any commercially available, general purpose microprocessor configured to execute and/or process instructions and data stored in a memory 206. The processor 204 may be coupled with the various components of the meter 200, and in general may direct and enable the functionality provided by the meter 200.

Memory 206 may be any computer-readable memory, such as a magnetic, optical, or semiconductor memory. Memory 206 may be implemented using a fixed memory device (e.g., flash) or a removable memory device, such as a memory card. In various aspects, the memory 206 may include one or more regions of a non-volatile memory (e.g., a ROM or flash memory), one or more regions of a volatile memory (e.g., RAM memory), or a combination of both. Memory 206 may include stored instructions or algorithms which, when executed by the processor 204, configure the meter 200 to perform various operations described below. Furthermore, the processor 204 may store, retrieve, and process various data in the memory 206, such as information received via an input interface 210, information output to a display 208, or information obtained and/or measured via port 202 during operation of the meter 200.

The input interface 210 may provide a mechanism for a user to interact with the meter 200. For example, the input interface 210 may include a power switch for activating the meter. The input interface may also include one or more additional buttons for enabling the user to operate the meter, such as a button for directing the start of a new test or retrieving results obtained during previous tests.

The display 208 may be any display suitable for presenting information to a user. For example, the display 208 may include an LED or LCD display, a graphics display, a plasma display, a backlit display, a touch screen display, or a combination segmented/graphic display. In an embodiment where the display 208 is a touch screen display, the display 208 may also be used by a user to provide inputs to the meter. The information displayed by the processor 204 on the display 208 may be in the form alpha/numerical characters and/or images stored in the memory 206, and may include one or more icons representative of one or more types of information provided (or received) by the meter. Some of the information that may be displayed to a user includes analyte concentration readings, time and date indicators, hematocrit readings, markers, error or alarm information, and any combinations thereof. For example, one or more error messages may be output to the display 208, which may include an error message that is displayed upon detection of a previously inoculated test strip. As another example, a glucose reading may be displayed upon the display 208 upon successful completion of a test without any errors.

The meter 200 according to this embodiment also includes a temperature sensor (e.g., a thermistor or a thermocouple) 212. The temperature sensor 212 is arranged to measure and provide an ambient temperature reading which represents the ambient temperature of the environment surrounding the meter. The processor 204 may periodically receive the ambient temperature readings and store the readings into memory 206 for further processing.

The meter 200 also includes a signal generator and measurement unit 214. Unit 214 is electrically coupled to strip port 202, so that unit 214 will be electrically connected to the electrodes of the test strip when the test strip is inserted into the meter. Unit 214 is arranged to apply electrical voltages between the electrodes of the test strip as discussed below, and to measure the currents flowing between the electrodes as also discussed below. Unit 214 may include conventional electronic elements such as regulated voltage sources, switches for connecting such sources to appropriate contacts in strip port 202, and conventional current measuring elements.

As further discussed below, unit 214 can measure each current flow at a series of measurement times, and can provide a signal representing the magnitude of the current at each measurement time. These signals typically are provided in digital form, and may be provided directly to processor 204 or stored into the memory 206 for further processing by the processor 204.

In a method according to one embodiment of the invention, a test strip 100 is engaged in strip port 202. Processor 204 performs an initialization routine which may include diagnostic tests of the meter components, and may also include an initial check of the test strip. In this initial check, unit 214 applies a low voltage as, for example, a few hundred millivolts, between the working electrode 102 and counter electrode 104, and monitors the current flowing between these electrodes. Because no liquid has been applied to the strip at this stage, and because reagent 118 should be dry and substantially non-conductive, there should be essentially no current flow. If the current flow between electrodes 102 and 104 exceeds a threshold value, this indicates that the strip is moist with fluid from a previous use of the strip. If this condition exists, processor 204 issues an error message through display 208 and terminates the test process. The processor then actuates unit 214 to apply a low voltage between the bare electrode 106 and the counter electrode 104. Here again, if the current exceeds a threshold value, this indicates the presence of moisture from a previous use of the test strip, and the processor issues an error message. It should be noted that these steps will not detect a used test strip which has been dried after use. A dried used test strip will exhibit high resistance and low or zero current flow between the electrodes during the steps mentioned above. A previously-used and dried test strip can be detected using additional steps discussed below.

If the error condition does not occur, the processor places the meter in a ready state. In this ready state, a message instructing the user to apply a liquid sample is displayed, and unit 214 applies a low voltage between bare electrode 106 and counter electrode 104, and repeatedly monitors the current flow. A sample of a liquid to be analyzed, such as blood or a control solution containing a known amount of glucose, is applied to the inlet opening 96 of channel 92. When the current flow between electrodes 104 and 106 rises above a threshold, this indicates that a sample has been applied to the test strip 100. The processor 204 initiates a timer, and instructs unit 214 to apply a low voltage between the working electrode 102 and detection electrode 107. When the current flow between these electrodes rises above a threshold value, this indicates that the fluid has filled channel 92 to the detection electrode 107, and thus has completely covered those portions of the working electrode 102 and counter electrode 104 disposed within the channel 92. If the timer initiated by the processor 204 reaches a maximum value before this occurs, this indicates that the fluid sample has not properly filled the channel 92. The processor 204 may issue an error message or instruct the user to apply more sample fluid. If the timer does not reach the maximum value before the fluid fills the channel 92, the system is ready for the glucose and hematocrit measurement routine.

When a fluid sample such as blood or a control fluid fills the channel and contacts the dry reagent 118, components of the dry reagent including the enzyme and the mediator disperse in the fluid. The glucose in the sample reduces the enzyme, and the enzyme in turn reduces the mediator. Thus, the sample contains reduced mediator at a concentration related to the concentration of glucose in the sample. The meter applies an electrical potential between the working electrode 102 on the one hand and the counter electrode 104 and detection electrode 107 on the other hand. In this stage of the process, the detection electrode 107 is electrically connected to the counter electrode 104 and acts as a part of the counter electrode. The applied potential oxidizes the mediator in contact with the working electrode. That is, the reduced mediator gives up electrons to the working electrode. This results in a current flow, referred to herein as the output current flow in response to the applied potential. The output current flow is related to the amount of reduced mediator present, and hence to the amount of glucose in the fluid sample. As is also known in the art, the output current flow typically decreases with time during application of the potential. The electrical potential may be applied as a single continuous potential or in multiple pulses, and measurement of the current flow may include a single measurement or multiple measurements. In further known variants, the potential may be applied as an alternating potential, resulting in an alternating current flow. As is also known in the art, current flow of this nature is also influenced by other factors such as temperature and the hematocrit of the sample, i.e., the percent of blood volume occupied by blood cells.

Figure 3:
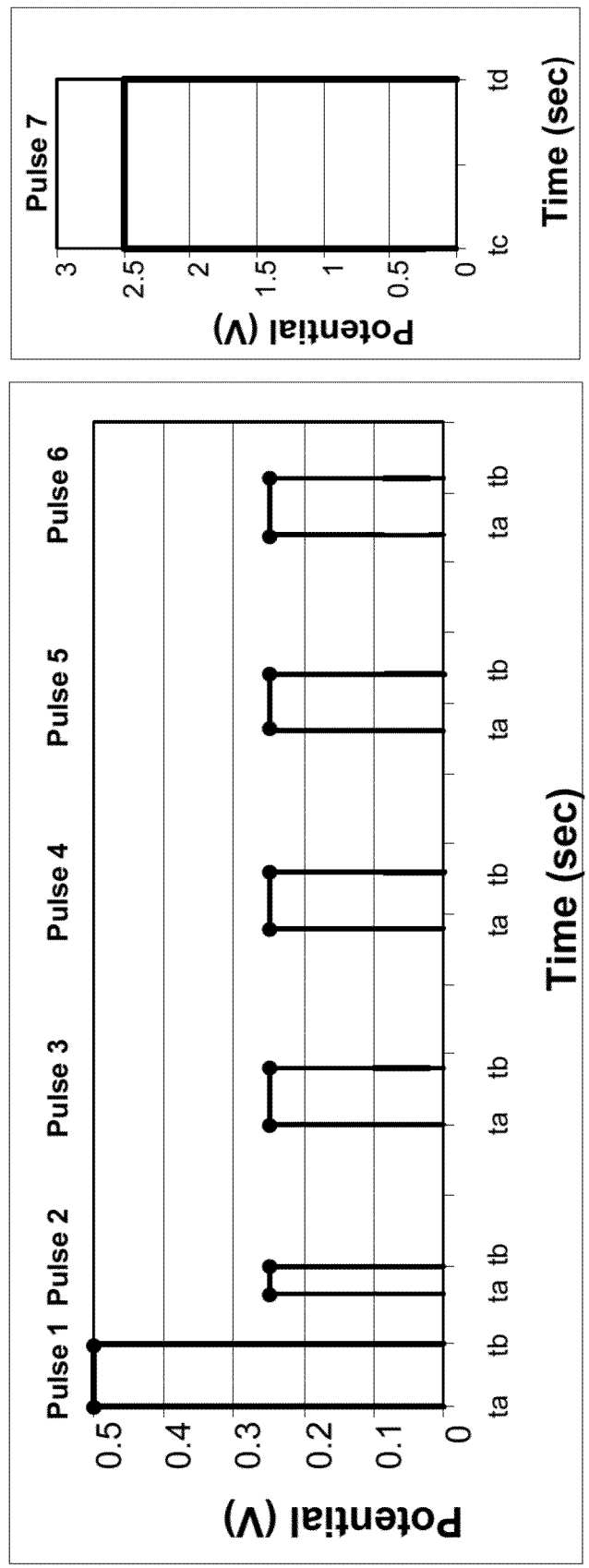
FIG. 3 is a graph of voltage versus time depicting a series of input pulses applied by the meter to the test strip during a method in accordance with one embodiment of the invention.

Merely by way of example, as shown in FIG. 3, the meter 200 may apply an input signal consisting of a series of input electrical potentials ("input pulses") shown as Pulse 1 to Pulse 6. Each of the input pulses may be sequentially applied for a time period tA to tB, where tA indicates the start time at which the electrical potential (V) is applied between the working and the counter electrode and tB indicates the time at which the electrical potential is removed. Each of pulses 1 through 6 typically is less than a second long. The potential applied during each of these pulses typically is, for example, about half a volt or less. As further illustrated, there may be a rest period between each of the input pulses during which time there is no potential that is applied across the working electrode 102 and the counter electrode 104.

Unit 214 measures an output signal consisting of the magnitude of the current flowing between the working electrode 102 and the counter electrode 104 at various times, and passes these values to the processor 204. For example, the meter may initially measure the output current flowing between the working electrode and the counter electrode at or shortly after the application of an input pulse at time tA, when the resulting output current may be at its greatest value for the given time period. The meter may continue to periodically measure the resulting (and decreasing) values of the output current at various times during the time period during which the input pulse is applied, with the last reading being at or about the time tB when the input pulse is removed across the working and the counter electrode.

Promptly after the end of Pulse 6, the last pulse applied between the working electrode and the counter electrode, the processor 204 commands unit 214 to apply a potential between the bare electrode 106 and one or more of the other electrodes of the test strip 100, such as the working electrode 102 or the counter electrode 104, and to monitor current flow between the bare electrode and the other electrode. Here again, detection electrode 107 acts as part of the counter electrode 104. As noted previously, the bare or hematocrit electrode 106 is located proximate to, yet separate from the working electrode 102 and the counter electrode 104, and outside the region 118 incorporating the dry reagent. Therefore, the current flow between the bare electrode 106 and the working electrode or counter electrode is not influenced by the concentration of glucose in the same manner as the current flows between the working electrode and counter electrode in the earlier pulses. The current flow between the bare electrode and the working or counter electrode is relatively insensitive to glucose in a bodily fluid such as blood, but is sensitive to the hematocrit.

In FIG. 3, the electrical potential applied between the bare electrode 106 and the working or counter electrode is depicted as Pulse 7. Pulse 7 may be applied for a time period tC to tD (e.g., 0.4 seconds), where tC indicates the start time at which the electrical potential is applied and tD indicates the time at which the electrical potential is removed. The potential applied between the bare electrode 106 and the working or counter electrode typically is greater than the potentials applied between the working electrode and counter electrode. For example, the potential applied to the bare electrode may be on the order of 2-3 volts.

Figure 4:
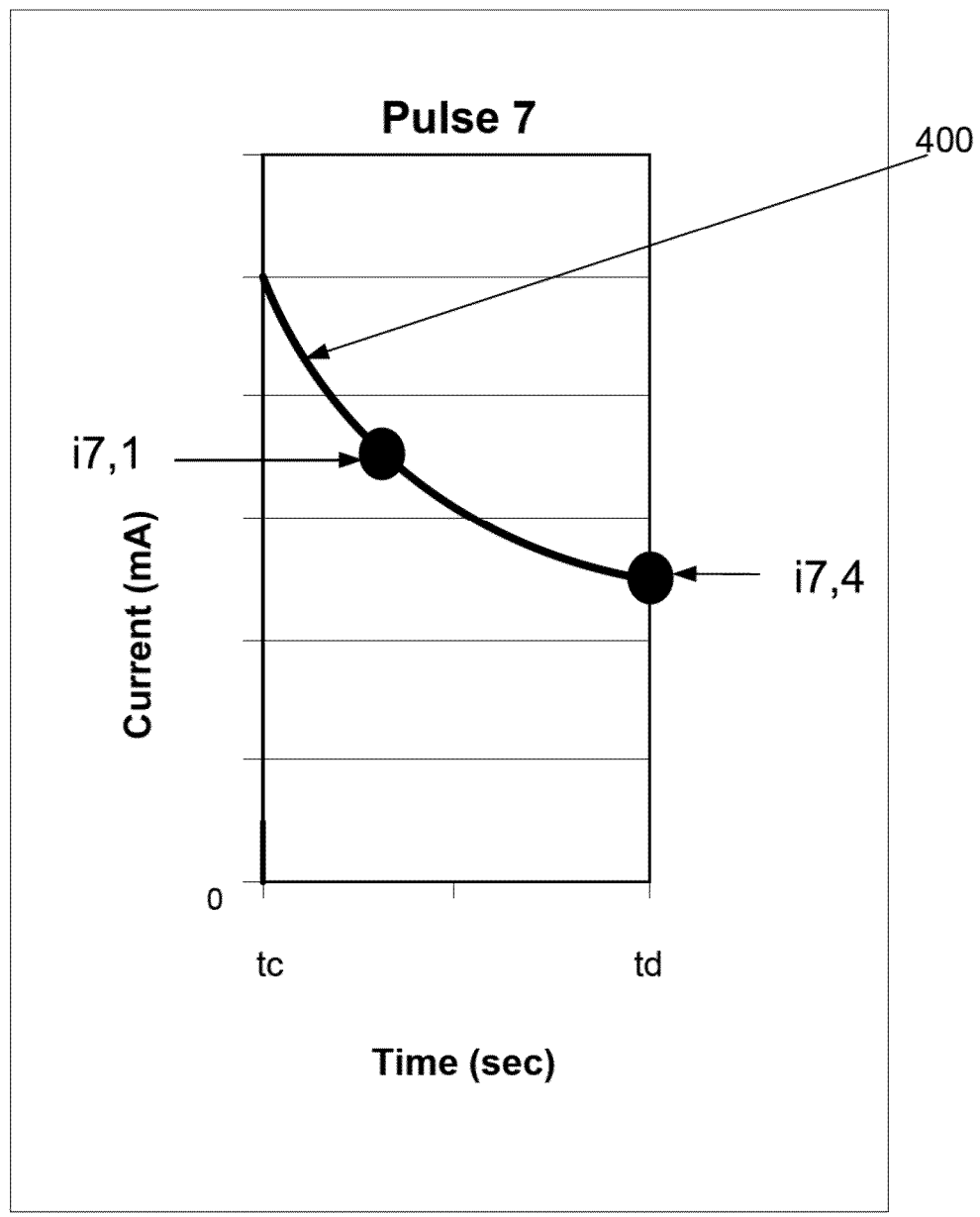
FIG. 4 is a graph of current versus time depicting an example of output current between electrodes of the test strip during the method of FIG. 3.

As shown in FIG. 4, the resultant output current flow 400 between the bare electrode 106 and either the working electrode 102 or the counter electrode 104 in response to the applied electrical potential may be measured at various times by the meter. For example, the unit 214 may initially measure the resulting output current at time t1, 0.1 second after the inception time tC of the pulse. The meter may continue to periodically measure the output current at various times while Pulse 7 is applied, where the last reading is taken at time at or about the time tD when Pulse 7 is removed.

Processor 204 uses the information obtained from the measurements described above, in conjunction with other information such as the ambient temperature as measured by sensor 212 and a calibration factor associated with the test strip to derive a value of the glucose concentration in the sample. For example, a raw estimate of glucose concentration can be calculated from a single one of the currents measured during pulses 1-6, whereas an estimate of hematocrit can be derived from one or more of the currents measured during pulse 7 and the ambient temperature, with or without additional information. The raw estimate of glucose can be corrected for hematocrit based on the estimate of hematocrit. The corrected glucose estimate may be further refined based on factors such as the various current values measured during pulses 1-6 and the ambient temperature. Numerous algorithms for calculating and correcting glucose concentrations are known in the art, and any such algorithm may be employed.

Processor 204 also executes a routine to determine whether the test strip 100 is previously used and dried test strip based on measurements of the output current 400 resulting in response to Pulse 7, i.e., the output current resulting from application of a potential between the bare electrode 106 and either the working electrode 102 or the counter electrode 104.

In accordance with this aspect, the processor 204 uses a first current value measured at a first time during application of the potential between the hematocrit electrode 106 and the working electrode 102 or counter electrode 104, and a second current value measured at another, later time during such potential application. For example, as shown in FIG. 4, the output current 400 may have a first value, referred to herein as i7,1, measured at or about shortly after the beginning time tC of Pulse 7. For example, i7,1 may be measured about 0.1 seconds after the potential is applied in pulse 7. The second or another current value, referred to herein as i7,4, may be measured about 0.4 seconds after the beginning time tD of pulse 7, i.e., at or near the end of the pulse. As shown in FIG. 4, the output current 400 during Pulse 7 decrease progressively, so that i7,4 is less than i7,1.

The present disclosure is not limited to any specific instances of the measurement times; measurements taken at other times during the potential application can be used as the first and second current values.

Processor 204 calculates a ratio between the first and second current values. For example, the processor may calculate the ratio of the second current value divided by the first current value. In the example discussed above, this ratio is (i7,4)/(i7,1), and this ratio is designated as R7 herein. The ratio between the first and second values observed with previously used and dried test strips differs markedly from the ratio observed with normal, unused test strip. For example, the measured R7 values are abnormally low for previously used and dried test strips that have been re-wetted with blood when compared to the corresponding measured values of normal test strips. The designation "previously inoculated" test strip is also used herein to refer to test strips which have been previously wetted with a liquid (e.g., blood or water) and then dried. This phenomenon is illustrated in graph 500 of FIG. 5, in which measured values of i7,4 and R7 for three types of blood-inoculated test strips including normal or previously un-inoculated test strips, dried test strips previously inoculated with blood, and dried test strips previously inoculated with water at a given ambient temperature have been plotted.

Figure 5:
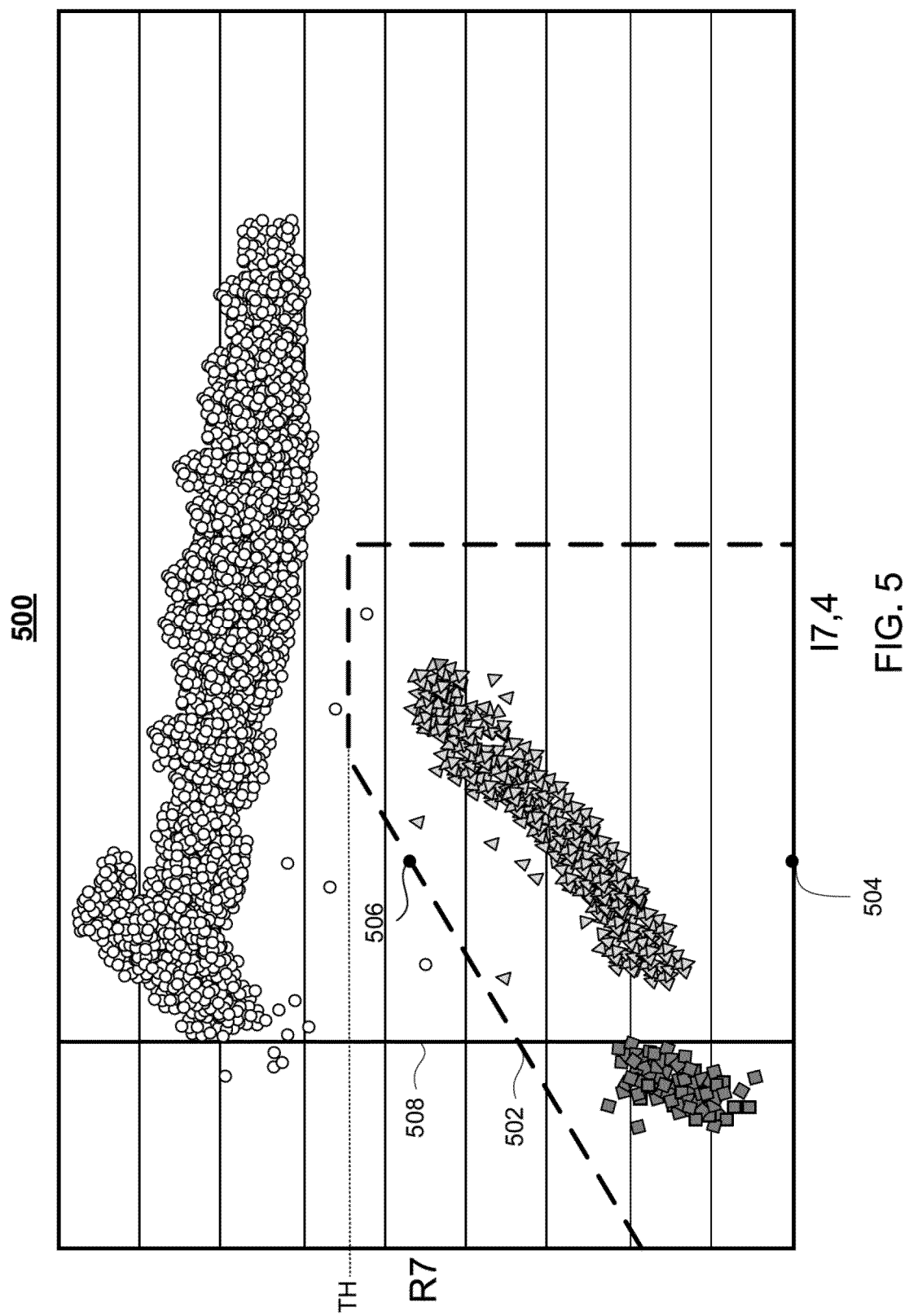
FIG. 5 is a graph depicting certain results measured using the method of FIG. 3.

As seen in FIG. 5, the measured R7 values for each of the three types of blood-inoculated test strips are plotted on the vertical axis of graph 500, with the corresponding i7,4 values that resulted in the R7 values being plotted on the horizontal axis of the graph. In particular, the measured R7 and i7,4 values obtained by testing blood-inoculated test strips using a number of normal (or previously un-inoculated), test strips are plotted using circles. The measured R7 and i7,4 values obtained by testing blood-inoculated test strips using dried test strips that were previously inoculated with blood are plotted using squares. Finally, the measured R7 and i7,4 values obtained by testing blood-inoculated test strips using dried test strips that were previously inoculated with water are plotted using triangles. As seen in graph 500, the measured R7 values for the previously used and dried test strips (represented by the triangles and squares, respectively) are generally lower compared to the measured R7 values for the normal test strips (represented by the circles).

As can be appreciated from FIG. 5, when blood is being tested in a particular test strip, comparison between the value of ratio between the first and second current values and a fixed ratio threshold value TH would provide good discrimination between normal and previously-used test strips. Stated another way, in this approach the ratio R7 resulting from a particular test using blood is compared to a fixed threshold value TH. If the value of R7 is greater than TH, the test is regarded as having been conducted with a normal test strip that had not been previously used. If the value of R7 is below TH, the test is regarded as having been conducted with a previously used and dried test strip.

However, even better discrimination can be achieved using a ratio threshold value which is a function of one of a current value measured during application of the potential between the bare electrode and another electrode. The ratio threshold value shown by point 506 on dashed curve 502 is a function of the second current value i7,4 (indicated as 504). The ratio threshold value increases with the second current value i7,4 over a range of second current values and remains constant for second current values above the range. The exact values of the ratio threshold function resulting in the curve 502 will vary with the configuration of the test strip, with the particular times of when the first and second current values are measured, and with other factors related to the meter and test strip configuration. However, for a test strip of a given configuration and a meter of a given configuration, the ratio threshold curve 502 can be determined by actual measurement using test strips meeting known conditions, i.e., used or unused and blood or control fluid. The ratio and second current value obtained with previously-used dried test strips and normal test strips in numerous tests are plotted in the same manner as shown by the curve 502 in FIG. 5. Using such a plot a ratio threshold function which gives good discrimination can be determined by inspection. Once the ratio threshold function (or functions) is established in this manner using a prototype meter of a given configuration, the ratio threshold function (or functions) can be stored in other meters having the same configuration made in a mass production operation. The function defining the ratio threshold is stored in the memory 206 of meter 200, either as a lookup table giving a specific threshold value for the ratio R7 for a given value of the second current i7,4 or as a set of parameters which allow calculation of the threshold for a given second current i7, 4.

The second current value typically varies with ambient temperature. For a given meter and test strip configuration, the relationship between the second current value and ambient temperature is constant. Thus, a given second current value or i7,4 measured at a known ambient temperature corresponds to a normalized second current value at a nominal operating temperature. A lookup table relating measured second current value and measured ambient temperature to the normalized second current value at nominal temperature can be compiled by actual test and used. Alternatively, the same information can be provided as parameters of a normalization function relating measured second current value and measured ambient temperature to the normalized second current value at nominal temperature. The second current values or i7,4 used in the tests to determine a ratio threshold curve should be normalized using such a normalization function or lookup table. The values of i7,4 represented in FIG. 5 are normalized to a nominal operating temperature. The ratio between first and second current values or R7 typically is not sensitive to ambient temperature and therefore need not be normalized.

A fixed current threshold value 508, referred to herein as the "i7,4 threshold", for the second current value i7,4 may be used for further discrimination between measurements from dried test strips that were previously inoculated with blood (indicated by the squares) and dried test strips that were previously inoculated with water (indicated by the triangles). Here again, the i7,4 threshold will depend on the configuration of the instrument and test strip, but is fixed for a given configuration. The i7,4 threshold for a given configuration can be determined by actual measurement of a set of known samples as discussed above. Here again, the values of i7,4 desirably are normalized as discussed above. The threshold value of i7,4 is also stored in memory 206 of the meter.

As a result, dried test strips that provide i7,4 measurement values that exceed the i7,4 threshold value 508 may be determined to be inoculated dried test strips that were previously inoculated by water and have subsequently dried. Such test strips may be discriminated from other dried test strips that provide i7,4 measurement values that are, for example, less than or equal to the i7,4 threshold value 508, which may be determined to be inoculated dried test strips that were previously inoculated by blood and have subsequently dried.

In yet another aspect, the meter 200 may be configured to not only determine whether a given blood inoculated test strip is a normal test strip or a dried test strip, but also to determine whether a test strip is a control test strip. A control test strip, as described herein, is a normal, previously un-inoculated test strip that has been inoculated with a control solution such as, for example, an aqueous glucose control solution rather than blood. This aspect is now described with reference to FIG. 6.

FIG. 6 is similar to FIG. 5, except that FIG. 6 further illustrates a number of measurement values (indicated using ellipses) obtained from testing normal test strips inoculated with a control solution rather than blood. As illustrated in FIG. 6, measurements of control solutions using normal, previously-unused test strips (represented by the ellipses) can be discriminated from measurements resulting from both blood-inoculated normal test strips and blood-inoculated dried test strips. Such discrimination can be based on both the ratio threshold curve 502 and the current threshold value 508. More particularly, a given test strip may be determined to be a control test strip when a measured R7 value corresponding to a given i7,4 current value is greater than the applicable R7 value determined from the ratio threshold curve 502 for the given i7,4 current value, while, at the same time the given i7,4 current value is also less than the current threshold value 508. This is possible because measurements of control solutions may be configured to yield current values between the bare electrode 106 and the other electrode below those obtained from measurements of blood. In particular, the control test strips may be designed such that the second current or i7,4 values obtained by testing normal test strips that have been inoculated with a particular control solution are generally lower than the second current or i7,4 values resulting from testing normal test strips that have been inoculated with blood, while, at the same time, the measured R7 values obtained from testing such control test strips are greater than those resulting from testing dried test strips that were previously inoculated with blood or water and have subsequently dried.

It will be noted from FIG. 6 that the current threshold 508 allows for discriminating the control test strips that have been inoculated with a control solution (ellipses) from normal test strips that have been inoculated with blood (circles). Further, the same current threshold 508 also allows discrimination between dried test strips that were previously inoculated with blood (squares) from dried test strips that were previously inoculated with water (triangles). However, it will be understood that this is not a limitation, and that in other embodiments there may be two (or more) different current thresholds instead of a single current threshold 508, one of which may be used to distinguish control test strips from normal test strips, while the other may be used to discriminate dried test strips previously inoculated with blood from dried test strips previously inoculated with water.

In operation during the method discussed above, processor 204 obtains the ambient temperature from sensor 212 and obtains the measured first current value i7,1 and second current value i7,4 from unit 214. The processor calculates the measured ratio R7 between the measured first and second current values. The processor also determines the normalized value of i7,4 using the function or lookup table relating the measured second current value to the normalized value as discussed above. Using the normalized second current value i7,4, the processor determines the applicable boundary ratio value 506 for the ratio R7 using the lookup table or parameters defining the threshold function 502 (FIG. 5) as discussed above.

The processor then compares the measured ratio R7 with the applicable boundary ratio value of the threshold. The processor may also compare the normalized second current value i7,4 with the i7,4 threshold 508. If the measured ratio R7 is below the applicable boundary ratio value 506 of ratio threshold curve 502, the processor determines that the test strip which was used to take the measurement was a previously used and a dried test strip and not a normal test strip. In response to this determination, the processor issues an error signal to the user through display 208, inhibits display of the measured glucose value on the display, or both. If the measured R7 value is greater than the applicable boundary ratio value 506 of the ratio threshold curve 502, the processor determines that the test strip used in the test was a normal, unused test strip and not a dried test strip. In this case, the processor actuates the display 208 to display the glucose value without the warning discussed above. If the measured ratio R7 value is the same as the applicable boundary ratio value 506 for the ratio R7, the processor desirably treats the test strip as a dried test strip. In other variants, the processor may treat the test strip as a normal test strip, or may issue a warning that a determination as to whether the test strip is a used and dried test strip or a normal test strip cannot be made.

If the normalized value of the second current i7,4 is below (or less than) the i7,4 threshold and, the measured R7 value is, at the same time, above (or greater than) the applicable boundary ratio value of the ratio threshold curve 502, the processor determines that the test was conducted with a normal test strip inoculated with control solution (such as an aqueous glucose solution) rather than blood (FIG. 6). The processor actuates the display to indicate that a control solution, rather than blood, was tested.

The embodiments described above have been found to accurately detect previously used and dried test strips regardless of whether the dried test strips were previously inoculated with blood or water. Although the present invention is not limited by any theory of operation, it is believed the previous inoculation of the dried test strips redistributes the chemistry provided on the working electrode 102 and the counter electrode 104 within the predefined region 118 onto the bare electrode 106. This redistribution or bleeding of the chemistry from the working electrode 102 and the counter electrode 104 during the previous inoculation onto the bare electrode 106 is believed to create an anomalous signal in the current response to the pulse applied to the bare electrode, i.e., Pulse 7.

Because tests of blood using previously used and dried test strips can provide erroneous glucose values, the ability to detect previously used and dried test strips provides a valuable safety feature. Moreover, this feature can be provided without additional physical elements in the test strip or meter, and without taking any additional measurements during the test. As noted above, the current measurements during application of the potential to the bare electrode are already captured and used for determination of the hematocrit. Thus, the additional safety can be provided without adding any appreciable cost or any perceptible delay to the test. The additional time, if any, required for the processor to perform the calculations involved is insignificant.

Numerous variations and combinations of the features discussed above can be employed. For example, in the methods discussed above the ratio between the first current value and the second current value is the ratio of the second current value to the first current value, i.e. (i7,4)/(i7,1) or R7. The inverse ratio can be employed. Thus, the processor can calculate the ratio of the first current value to the second current value or (i7,1)/(i7,4) in the example discussed above. If the inverse ratio is employed, tests using normal test strips will yield a lower value than tests using previously inoculated and dried test strips. In the embodiments discussed above, the ratio threshold is a function of the second current value. However, the ratio threshold can be selected as a function of the first current value or another current value measured during the application of potential between the bare electrode and another electrode.

In the embodiments discussed above, a ratio between a first current measured at a first time during application of a potential between the bare electrode and another electrode and a second current measured at a later time during the same potential application is employed to discriminate between a normal test strip and a dried test strip. However, one or more other parameters of the current flow between the bare electrode and another electrode can be employed. The potential applied between the bare electrode and another electrode may be an alternating or varying potential rather than the constant direct potential applied in the example above.

In the example shown in FIG. 3 the potential between the bare electrode and another electrode (Pulse 7) is applied after the potentials between the working electrode and counter electrode (Pulse 1 to Pulse 6) are applied. In other embodiments, the potential may be applied to the bare electrode prior to the application of a potential between the working electrode and counter electrode. Yet further, the potential may be applied to the bare electrode during an interval between application of potentials between the working electrode and counter electrode (e.g., during a rest period between Pulse 1 and Pulse 2 in the example of FIG. 3). Application of potential to the bare electrode desirably does not occur at the same time at which other pulses are applied, because this may result in indeterminate results.

In the embodiment discussed above, the analyte is glucose, and the liquid of interest containing the analyte which is applied to the test strip is blood. However, the present invention can be applied in measurements of other analytes in other liquids. The test strips used for such other measurements contain other known reagents, most typically an enzyme reactive with the analyte and a mediator having a redox potential appropriate for use with the enzyme. These reagents are provided in dry form in a region of the test strip in the same manner as discussed above.

In other embodiments, an electrochemical measurement can include application of an input signal other than an electrical potential between electrodes and measurement of an output signal other than the current passing between the electrodes. For example, a current can be applied as the input signal and a potential can be measured as the output signal. In still other embodiments, the test strip can be arranged to conduct measurements other than electrochemical measurements.

In the embodiments discussed above, the bare electrode 106 (FIG. 1) is disposed proximal to the counter electrode 104 and working electrode 102. However, the bare electrode can be disposed distal to the working electrode and counter electrode along the channel 92. Other locations can also be employed, provided that the bare electrode lies in a location where it will be wetted by the liquid introduced into the tests strip, and lies outside of the region 118 covered by the dry reagent as applied during manufacture. Desirably, the bare electrode lies close to the working electrode and counter electrode.

In still other embodiments, the test strip can include two or more bare electrodes, both disposed outside of the region covered by the dry reagent. Both of the bare electrodes should be disposed in locations where the will be wetted by the liquid introduced into the test strip. In this embodiment, the potential applied between a bare electrode and another electrode may be a potential applied between two bare electrodes. Here again, one or more parameters of the current flow responsive to such potential will be different if a previously used and dried test strip is employed.

It is not essential to provide discrimination between tests using control solution and tests using blood, as discussed above with reference to the control solution threshold 508 (FIG. 6). This feature may be omitted entirely.

Although the present disclosure has been illustrated with reference to particular embodiments, it should be understood that these examples are merely illustrative of the principles and applications of the disclosure. Additionally, it should be understood that numerous other modifications may be made to the illustrative embodiments. However, these and that other arrangements may be devised without departing from the spirit and scope of the present disclosure as defined by the appended claims.

The invention claimed is:

1. A method for detecting reuse of a test strip in a biosensor, the method comprising:
    inoculating a test strip with a liquid, the test strip having a dry reagent and a plurality of electrodes including a bare electrode which is not in contact with the dry reagent in an unused condition of the test strip, the inoculating step being performed so that the liquid contacts the dry reagent, the bare electrode and one or more other electrodes;
    while the electrodes are in contact with the liquid, applying an electrical potential between the bare electrode and one or more of the other electrodes;
    measuring a current flow between the bare electrode and one or more of the other electrodes responsive to application of the potential; and
    determining, based on one or more parameters of the measured current flow, whether the test strip is one that has been previously wetted and dried before the inoculating step.

2. The method of claim 1, wherein the measuring step includes the step of measuring a first current value at a first time during the potential applying step and measuring a second current value at a second, later time during the potential applying step.

3. The method of claim 2, wherein the determining step includes:
    calculating a ratio between the second current value and the first current value; and
    comparing the ratio between the second current value and the first current value with a boundary ratio value.

4. The method of claim 3, further comprising:
    selecting the boundary ratio value based at least in part on a current value measured during the potential-applying step.

5. The method of claim 4, wherein the selecting step is performed based at least in part on one of the first and second current values.

6. The method of claim 3, wherein the ratio is the ratio of the second current value divided by the first current value, and the determining step includes determining that the test strip is one that had been previously wetted and dried when the ratio is less than or equal to the boundary ratio value.

7. The method of claim 1, wherein:
the one or more other electrodes on the strip include a working electrode a counter electrode.

8. The method of claim 7, further comprising:
applying at least one input electrical signal between the working electrode and the counter electrode;
measuring at least one output signal resulting in response from application of the at least one input electrical signal; and,
determining a concentration of an analyte in the sample based at least in part on the at least one output signal.

9. The method of claim 8, further comprising
correcting the determined concentration of the analyte in the sample based at least in part on at least one parameter of the measured current flow.

10. The method of claim 9, wherein the liquid is blood and the correcting step includes correcting the determined concentration for an effect related to hematocrit.

11. The method of claim 10, wherein the input electrical signal is a potential and the output electrical signal is a current flowing between the working and counter electrodes.

12. The method of claim 11, wherein the analyte is glucose and the dry reagent includes an enzyme reactive with glucose and a mediator.

13. The method of claim 1, further comprising:
comparing a current value measured during the potential-applying step with a threshold current value; and,
based on the comparison, determining whether the test strip is one that has been previously wetted with blood and dried before the inoculating step.

14. The method of claim 1, wherein the bare electrode extends across a flow channel of the test strip at a location proximal to a working electrode and a counter electrode, and outside a region occupied by the dry reagent.

15. A biosensor comprising:
a processor;
a memory storing one or more executable instructions, the instructions, when executed by the processor, configuring the processor to:
apply an electrical potential between a bare electrode and one or more other electrodes of a test strip while the electrodes of the test strip are in contact with a liquid, the test strip having a dry reagent, wherein the bare electrode is not in contact with the reagent in an unused condition of the test strip;
measure a current flow between the bare electrode and one or more of the other electrodes responsive to application of the potential; and
determine, based on one or more parameters of the measured current flow, whether the test strip is one that has been previously wetted and dried before inoculation of the test strip with the liquid.

16. The biosensor of claim 15, wherein the processor is configured to:
measure a first current value at a first time during the potential applying step;
measure a second current value at a second, later time during the potential applying step;
calculate a ratio between the second current value and the first current value; and
compare the ratio between the second current value and the first current value with a boundary ratio value.

17. The biosensor of claim 15, wherein the bare electrode extends across a flow channel of the test strip at a location proximal to a working electrode and a counter electrode, and outside a region occupied by the dry reagent.

18. A non-transitory computer-readable storage unit on which computer readable instructions of a program are stored, the instructions, when executed by a processor, causing the processor to:
apply an electrical potential between a bare electrode and one or more other electrodes of a test strip while the electrodes of the test strip are in contact with a liquid, the test strip having a dry reagent, wherein the bare electrode is not in contact with the reagent in an unused condition of the test strip;
measure a current flow between the bare electrode and one or more of the other electrodes responsive to application of the potential; and
determine, based on one or more parameters of the measured current flow, whether the test strip is one that has been previously wetted and dried before inoculation of the test strip with the liquid.

* * * * *

UNITED STATES PATENT AND TRADEMARK OFFICE
CERTIFICATE OF CORRECTION

PATENT NO. : 9,164,056 B2  
APPLICATION NO. : 13/600441  
DATED : October 20, 2015  
INVENTOR(S) : Bern Harrison Page 1 of 1

It is certified that error appears in the above-identified patent and that said Letters Patent is hereby corrected as shown below:

IN THE SPECIFICATION

In Column 2, Line 57, delete "electrode" and insert -- electrode and --, therefor.

In Column 4, Line 53, delete "electrode 104." and insert -- electrode 102. --, therefor.

In Column 14, Line 7, delete "the" and insert -- they --, therefor.

IN THE CLAIMS

In Column 15, Line 5, in Claim 7, delete "electrode" and insert -- electrode and --, therefor.

In Column 15, Line 14, in Claim 9, delete "comprising" and insert -- comprising: --, therefor.

Signed and Sealed this  
Ninth Day of August, 2016

Michelle K. Lee  
*Director of the United States Patent and Trademark Office*